United States Patent [19]

Thompson et al.

[11] 4,228,512

[45] Oct. 14, 1980

[54] NUCLEAR PULSE COUNTING APPARATUS AND TECHNIQUE

[75] Inventors: John W. Thompson; Arthur J. Kamp, both of Midland; Edward R. Sederlund, Saginaw, all of Mich.

[73] Assignee: The Dow Chemical Company, Midland, Mich.

[21] Appl. No.: 902,312

[22] Filed: May 3, 1978

[51] Int. Cl.² ............................................. G06F 15/46
[52] U.S. Cl. ................................... 364/527; 364/555; 364/498
[58] Field of Search ................ 364/527, 414, 555, 498

[56] References Cited

U.S. PATENT DOCUMENTS

| | | | |
|---|---|---|---|
| 3,435,239 | 3/1969 | Stalberg | 364/527 X |
| 3,515,861 | 6/1970 | Nather | 364/527 X |
| 3,578,960 | 5/1971 | Georgi et al. | 364/527 |
| 3,872,287 | 3/1975 | Koeman | 364/527 |
| 3,925,644 | 12/1975 | Bergman et al. | 364/527 X |
| 4,133,039 | 1/1979 | Eichenlaub | 364/300 X |

Primary Examiner—Edward J. Wise

[57] ABSTRACT

A nuclear pulse counting experiment, such as typified by the art of X-ray fluorescence empolys a multichannel analog to digital converter (ADC) which is interfaced with a microprocessor to yield sample/matrix concentration data, as an illustrative example, with a precision which is given by the theoretical nuclear decay statistical limits. In specific regard to X-ray fluorescence analysis, the ADC characterizes each pulse or count according to magnitude without conventional backscatter peak gain stabilization. The data is transferred through a buffer to the microprocessor, which scans the higher energy characterizations for maximum count, identifies that characterization as the peak, ± 1 characterization, and interpolates to develop a refined backscatter peak, stated to at least 1/10 of a characterization, and from which data base all ensuing calculations are predicated.

5 Claims, 5 Drawing Figures

NUCLEAR PULSE COUNTING APPARATUS AND TECHNIQUE

FIELD OF THE INVENTION

The invention is in the field of nuclear pulse counting experiments such as exemplified by X-ray fluorescence analysis. More particularly, the invention relates to an improved combination of hardware and an improved technique for developing the pulse count data with unusually high precision, and also in a beneficial manner which assures a broader possible application of the technology less critically dependent on the selection of the radiation source.

BACKGROUND OF THE INVENTION

Nuclear pulse counting experiments, of which X-ray fluorescence analysis is exemplary, in principle, sorts radiation counts according to magnitude and tabulates the counts in each magnitude or energy characterization. The count data on a statistical basis is used to calculate, for example, sample/matrix concentrations.

Generally typical systems of the kind involving nuclear pulse count analysis employ the combination of a count detector, stepwise amplification of the counts, and count sorting, tabulation, and calculation functions. In typical X-ray analysis, for example, most commonly two, and possibly up to four, energy characterizations are employed to sort the counts. Since the backscatter and fluorescence peaks are mathematically related, preferred modes identify the more prominent backscatter peak, and from that data compute the position of the fluorescence peak. The mode of identifying the backscatter peak is most often by peak stabilization techniques accomplished through gain factoring methods. Thus normally, it will be observed that typical prior art systems rely on some form of an amplification gain stabilizer.

Disadvantages of such systems are unsuitability of the technique unless threshold count densities are established. Thus since gain stabilization is based on the principle of monitoring narrow "energy" windows on each side of the stabilized peak center line, insufficient count density necessary to produce a statistically reliable and balanced numerical count in each monitored area, develops conditions whereby the center line may meander. In such cases, the X-ray analytical technique is generally unsuitable, or may force the selection of a radiation source that is not optimum for the experiment.

Typical precision achieved by the prior methods may be expressed generally as about ±3% relative. Improvements over this number may be achieved by utilizing highly sophisticated detector forms, as exemplified by lithium/germanium detectors, with required liquid nitrogen cooling systems. However, the advantage of using the latter optimum detector form is frequently offset by the extreme damage prone and fragile nature of the detector. Such are thus oftentimes judged unsuitable for industrial applications, and substitution with less precise but otherwise more suitable scintillation detectors and/or proportional counters is usually preferred.

THE INVENTION

The invention departs from the traditional peak stabilization technique of nuclear pulse counting experiments in a particular manner that beneficially expands the possible applications of the technique, and particularly in the latitude of selection of the optimum radiation source for the experiment. In addition, using less than optimum detector forms, the principles applied in practicing the invention are suited to developing data of exceptionally good precision. More particularly, the invention is predicted on sorting of amplified charge pulses without resort to peak stabilization functions as typically practiced in the prior art in the form of gain factoring methods. Consequently, radiation sources generating very low count densities may be suitably employed in practicing the invention.

The pulse charges are sorted proportional to magnitude using a multichannel analog to digital converter of at least 128 channels, i.e., characterizations, and more preferably 256 characterizations are required by the system. The sorted counts are transferred at a random frequency to a buffer or interface, and therefrom at a regulated frequency to a data processor, as for example, a microprocessor or mini-computer. The computer performs energy discriminating, tabulation, and calculation functions. The preferred program requires the data processor to scan certain of the higher energy characterizations to identify that characterization of the highest energy count to an accuracy of ±1 characterization. That characterization is then defined as the peak center line and refined to at least 1/10 of a characterization by interpolating techniques. In the preferred mode of X-ray fluorescence analysis, the shoulders of the backscatter peak and the shoulders of the fluorescence peak are defined by experiment and fed into the computer program. This information together with the thusly arrived at identity of the backscatter peak center line (and the therefrom deducible fluorescence peak center line) quantifies with high accuracy and without need for peak stabilization functions, the exact boundaries within which the fluorescence and backscatter counts should be tabulated. The technology is demonstrated to be extremely precise even under drastic conditions of purposely induced amplification gain fluctuations as documented below. In addition, the preferred interface which eliminates essentially all dead time of the data processor, and the preferred program for practicing the technology, are illustrated below.

In reference now to the detailed description of the preferred embodiment of the invention, reference is taken to the accompanying drawing of such preferred embodiment, wherein.

DETAILED DESCRIPTION OF THE PREFERRED EMBODIMENT

Figure 1:
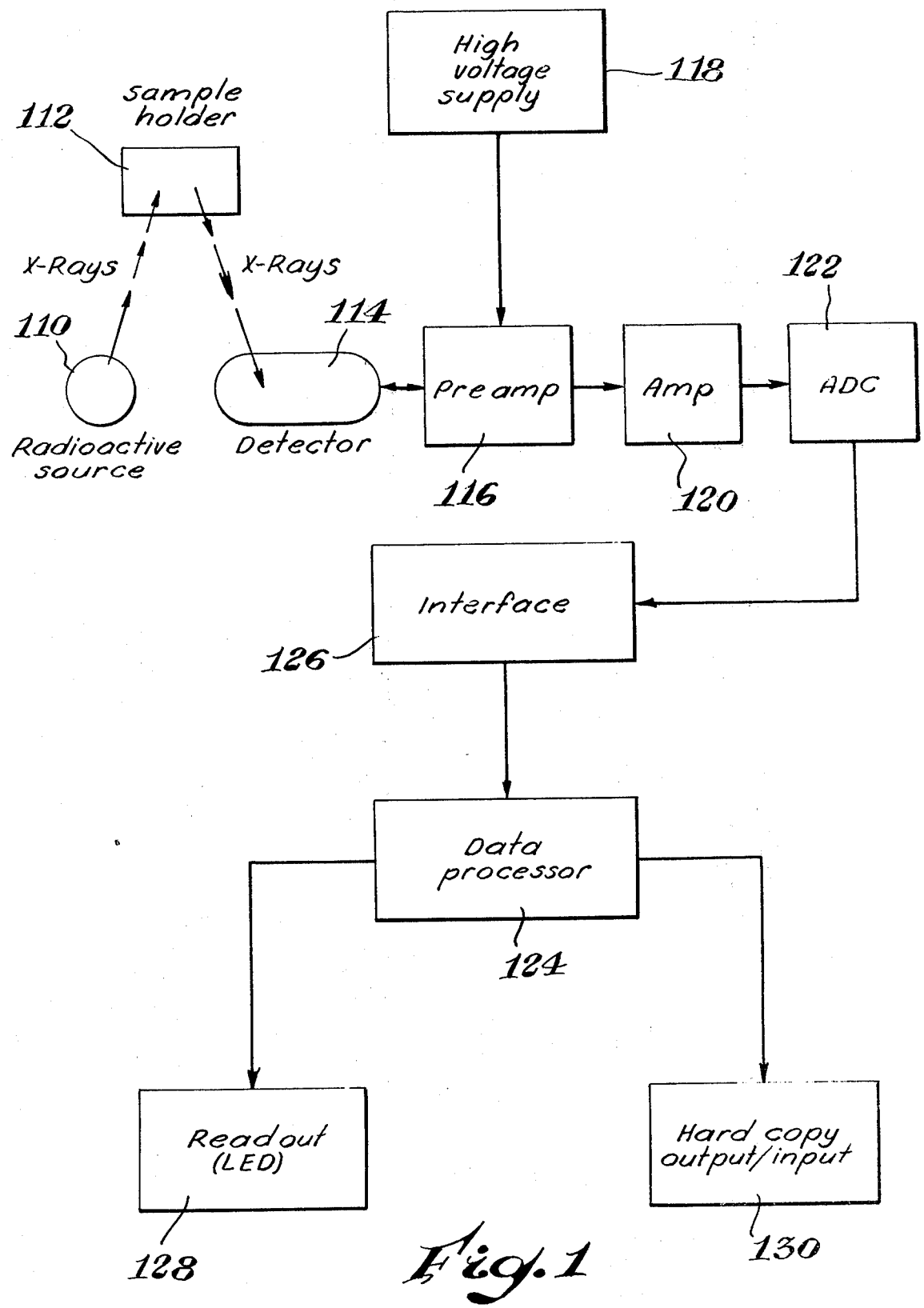
FIG. 1 is a schematic and diagrammatic view of an X-ray fluorescence analyzer coupled with an analog to digital converter, buffer, and data processor according to the mode contemplated by the principles of the invention.

The setup for an X-ray fluorescence analyser, contemplated by the invention is illustrated in a classical and preferred form in FIG. 1. The apparatus includes the conventional and prior known elements of a suitable radioactive source 110, sample/matrix holder 112, and detector 114. The detector generates a charge "pulse" in the conventional mode which is stepwise amplified, and the pulse shaped using a preamplifier 116, with an associated high voltage power supply 118. The preamplified signal is thusly supplied to an amplifier 120. The brackets set about the above described elements delineates the same as a prior system, of which various functionally equivalent forms are available and known, and which may be employed beneficially in conjunction with the present inventive practices and apparatus.

The invention thus most particularly relates to a multichannel analog to digital converter (ADC) 122 interfaced operationally with amplifier 120, and in turn, interfaced operationally to a data processor, i.e. microprocessor or micro-computer 124, through an interface or buffer device 126. The output of the data processor is reported by a suitable visual display device such as a strip chart recorder or numerical LED (light emitting diode) display 128. Optionally, a hard copy display such as a teletype 130 may be connected in tandem with device 128.

The Buffer

Figure 2:
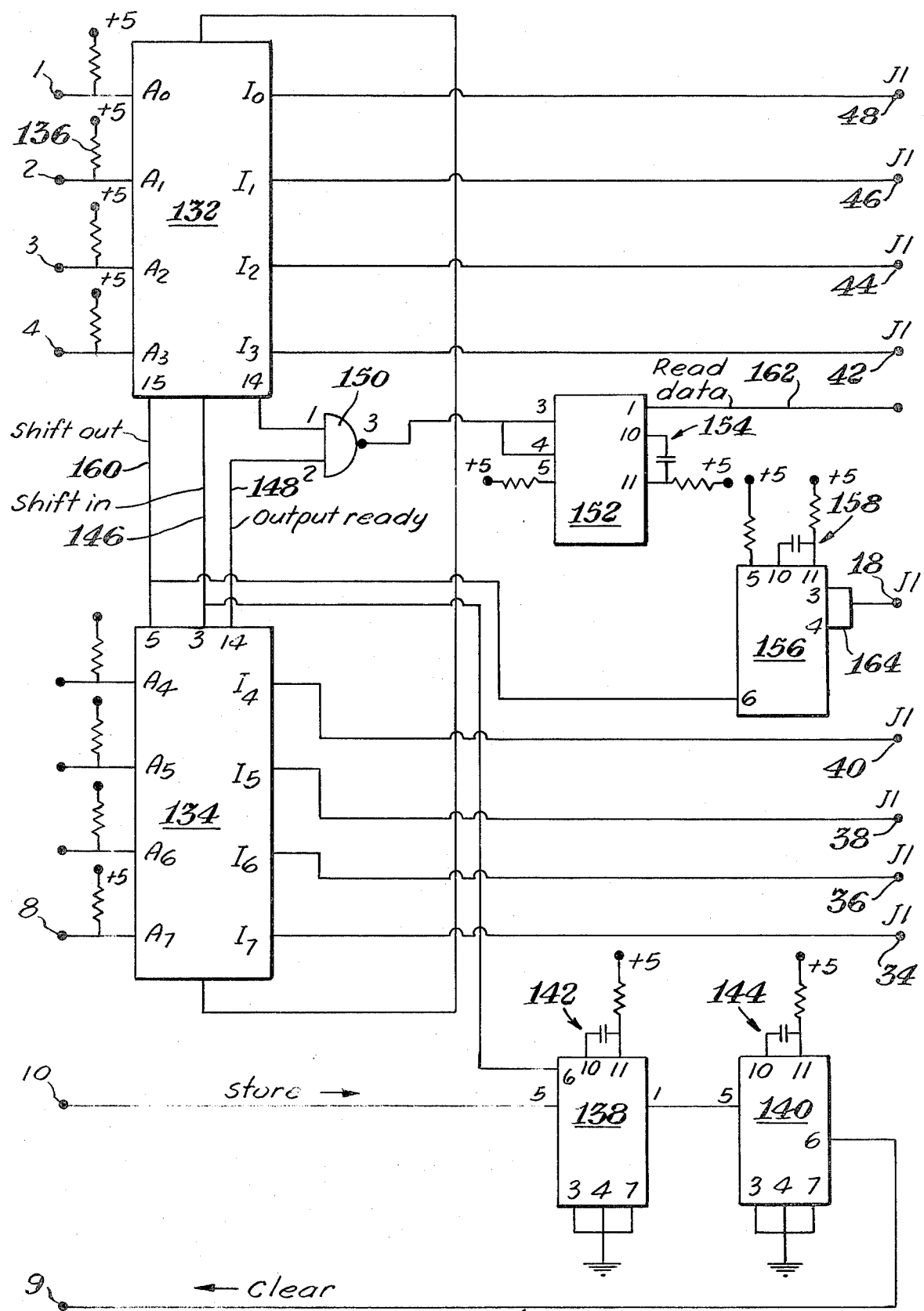
FIG. 2 is a circuit diagram illustrating the construction of the buffer used in the FIG. 1 apparatus.

The interface element 126, supra, is shown in detail in FIG. 2. In this respect the drawing is described with regard to a preferred Tracor Northern Model HEI-01, analog to digital converter. The preferred data processor, element 124, in conjunction comprises an Intel SBC 80/20 micro-computer. Hence, certain of the assigned number designations given have meaning with respect to the schematics of these instruments as supplied by their respective manufacturers, and may thus be conveniently used in duplicating the present preferred design.

The interface 126 comprises a pair of Fairchild Model 3341, 64 by 4 bit, first in/first out (FIFO) buffers 132, 134. The buffers 132, 134 define input terminals designated $A_O$-$A_7$ (non-manufacturers' designation). The terminals are each held at +5 volts through pull-up resistors 136. Terminals $A_O$-$A_7$ are connected to the respective outleads or output lines 1-8 (manufacturers' designation, hereinafter-md-) of the above-identified Tracor ADC. The buffer 132, 134 outputs, non-manufacturers' designation $I_O$-$I_7$, are connected to the input terminals $J1_{48}$ through $J1_{34}$ (md), even number subscripts only, of the Intel micro-computer 124.

The ADC, in addition, includes output lines 9, 10 (md), shown at the lower left hand part of the drawing. The ADC output No. 10 is connected to Pin No. 5 (md) of a Texas Instruments SN 74121N Monostable Multivibrator or one-shot 138 (all Pin Nos. below corresponding to the manufacturers' designation). A first output, Pin No. 1, of the monostable multivibrator 138 is connected to Pin No. 5. of a second monostable multivibrator 140 of the same design and origin. Pin No. 6 of the second multivibrator is connected to line No. 9 of the ADC, hereinafter referred to as the ADC "CLEAR" line, and distinguished from line 10, hereinafter referred to as the "STORE" line.

Referring now to the various pin connections of the first and second multivibrators, Pin Nos. 10 and 11 are joined to RC networks 142, 144 respectively, each comprising a 10KΩ resistor, and a 400 Pico farad capacitor. Pin Nos. 3, 4, and 7 are each grounded as shown. The second output, Pin No. 6, of the first multivibrator (distinguished from its first output, Pin No. 1, discussed supra) is connected to a "SHIFT-IN" input line 146, connecting between Pin Nos. 3, 3 of buffers 132, 134, respectively.

Referring now to the "OUTPUT READY" line, designated line 148 in FIG. 2, such is connected to Pin No. 14 of buffer 132 and to Pin No. 1 of a Texas Instruments SN7400N NAND gate 150. Pin No. 2 of the NAND gate, in turn, is connected to Pin No. 14 of buffer 134.

Pin No. 3 of the NAND gate is connected in parallel to Pin Nos. 3 and 4 of a third monostable multivibrator 152, of the preferred same design and origin as specified, supra. The third monostable multivibrator is connected via Pin No. 5 through a 2.2KΩ pull-up resistor to a +5 volt D.C. emf. Pin Nos. 10 and 11 of the third multivibrator are connected to an RC network 154, of a like type to that previously described, and comprising a 10KΩ resistor and a 400 Pico farad capacitor, the resistor being connected to a +5 volt D.C. emf. terminal. Pin No. 1 of the third multivibrator is connected to Pin No. $J1_{26}$ of the aforedescribed micro-computer, through a line 162, referred to as the "READ DATA" line.

A fourth monostable multivibrator 156, has Pin Nos. 3 and 4 connected to Pin No. $J1_{18}$ of the micro-computer, through line 164, hereinafter referred to as the "READ DATA ACKNOWLEDGE" line. Pin No. 5 is connected through a 2.2KΩ pullup resistor to a +5 D.C. emf.; and similarly Pin Nos. 10 and 11 are attached to an RC network 158 of the identical type as previously described. Pin No. 6 of the fourth monostable multivibrator 156 is connected to what is referred to as the SHIFT OUT line 160 between Pin Nos. 15, 15 of buffers 132, 134, respectively.

Data Gathering Cycle

The operation of the apparatus is now described. On each event of an X-ray or fluorescence ray entering the detector 114, i.e., detector window, a charge pulse is developed whose magnitude is proportional to the energy of the X-ray or fluorescence ray, as applies. Each thusly detected pulse is converted to a voltage pulse by the preamp 116, which is then amplified and shaped by amplifier 120 in the conventional and known mode.

The mode of the invention is thus distinguished based on the uniquely practiced signal characterization and counting steps, together with the below defined step of critical backscatter peak location. For this function, the ADC 122 sorts the pulses from amplifier 120 according to their height, i.e., energy, into one of several characterizations or energy windows. Using a 7 bit ADC, 128 characterizations are possible. The preferred 8 bit ADC, mentioned and described in detail above, produces 256 characterizations. No gain stabilization is required or preferably practiced.

The data is transmitted randomly to the interface 126. In respect to the specific data processor 124 used in the preferred system, and which is illustrative of the mode generally, the instruction sequence used to read the data into the computer requires approximately 37 microseconds. This translates into an average counting rate of 27,000 per second. However, the pulses from the amplifier are random and may occur at a much faster rate than the calculated average time. For example, a count rate of 10,000 counts per second would indicate an average pulse rate of $10^{-4}$ seconds. However, a burst of pulses can, and will likely occur at a faster rate than the data processor can manage, with a resulting lo:  of a percentage of the pulses. As illustrative exampl . at a rate of 10,000 c/s (aver.=1 count per 100μ sec.), about 26% of the pulses would fall within the 37μ second dead time range. Essentially, the buffer 126 will accept a data burst from the ADC, while allowing the data processor to strobe data out of the buffer at its own rate of approximately one data word every 37 microseconds. This results in no significant data processor introduced dead time as long as the 27,000 cps average count rate is not exceeded.

Figure 3:
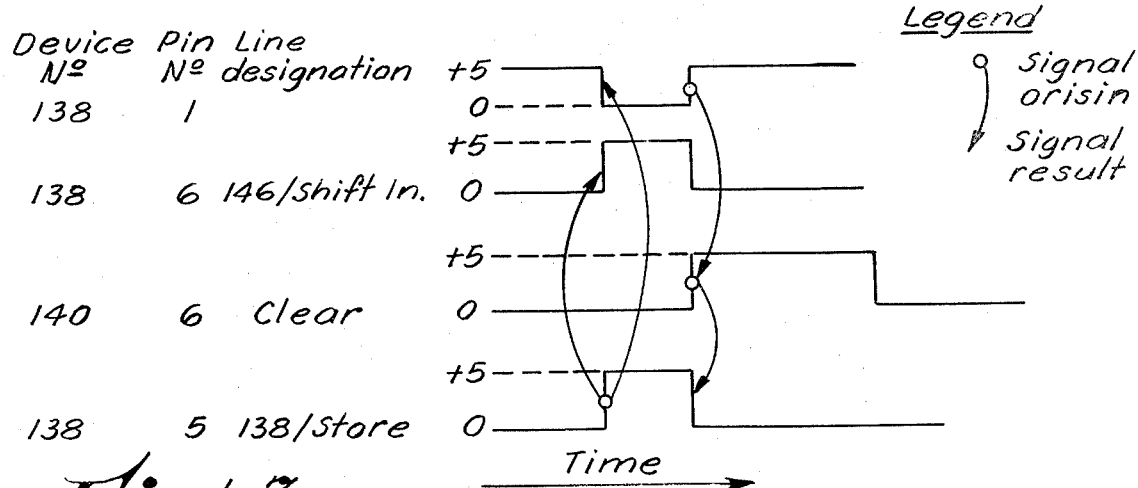
FIGS. 3 and 4 are timing diagrams, respectively, relevant to the mode of operation of the buffer of FIG. 1.

The sequence of performance of the buffer in the above-described function is now detailed with particular reference to the timing diagram of FIG. 3. In this sequence of events, the ADC presents the channel characterization numbers to the buffers 132, 134 at terminals $A_0$–$A_7$. When data is present in these lines, the ADC raises the STORE line 138 "high" (i.e., +5 volt D.C. emf.). This will cause the first multivibrator 138 to change its voltage level on Pin No. 1 from +5 to 0 volts momentarily, and back to +5 V which causes the second multivibrator 140 to change the voltage level on Pin No. 6 from 0 volts to +5 V D.C. emf., and back to 0 volts. The +5 V pulse clears the ADC of present data and allows another pulse analysis to be performed by the ADC.

At the same moment, Pin No. 1 of the first multivibrator 138 is changing from +5 to 0 volts, Pin No. 6 is changing from 0 to +5 V D.C. emf. and back to 0 volts. This change in voltage level is applied to the SHIFT-IN line 146 between Pin Nos. 3 of buffers 132, 134, causing the data present at terminals $A_0$–$A_7$ of the buffers to be read into the first four fit words of the buffer. A data word is thusly passed through the buffer to the last unoccupied 4 bit word automatically.

Figure 4:
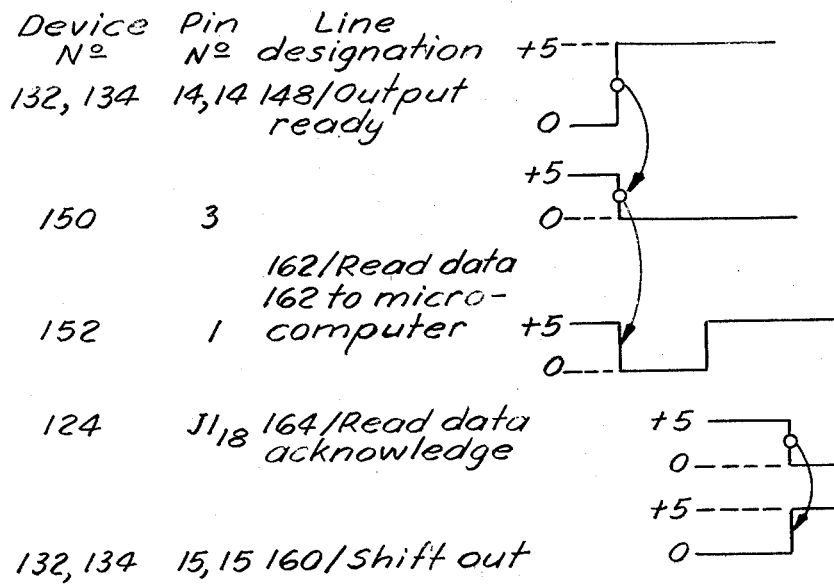

The reset timing sequence is diagrammed in FIG. 4. When a data word reaches the output stage of the buffer, it causes the OUTPUT READY line 148, Pin Nos. 14, to change from 0 volts to +5 V D.C. When both buffers 132 and 134 apply +5 volts D.C. to the inputs 1 and 2 of NAND gate 150, Pin No. 3 of the NAND gate changes voltage level from +5 V D.C. to 0 volt. This causes the third multivibrator 152 to change the voltage level on Pin No. 1 from +5 V to 0 V, and back to +5 V, signaling the micro-computer through DATA READ line 162 and terminal J1$_{26}$ that data is available for input. After the data has been inputed to the micro-computer using the instruction sequence outlined in Table I, below, the computer changes the voltage level on pin J1$_{18}$ from +5 to 0 volts and back to +5 V. This causes the fourth multivibrator 156 to change the voltage level on Pin No. 6 momentarily from 0 to +5 V. This pulse is applied to the SHIFT OUT line 160 between buffers 132, 134 which causes the output stage of the buffers to be reset. The next word that was input to the buffers is thus allowed to enter the output stage, where the process is repeated, thus feeding data to the micro-computer at a regulated speed.

The data gathering part of the cycle continues in the mode described for a designated time duration, or else the cycle to terminate data collection is based on a numerical number of counts being taken in certain of the defined energy characterizations or channels. Both modes are based on the statistical reliability of the numerical or probable numerical count.

Data Processing

The data is then processed using the preferred programming form defined by the neumonics of Table I. It will be observed that the preferred program is, of course, specific to the Intel SBC 80/20 model microcomputer preferred in these studies.

TABLE I

DATA INPUT INSTRUCTIONS in Intel ® 8080 Assembly Language Neumonics for use with Intel ® SBC 80/20 Microcomputer

|  | IN | DATA | ; Input Data Byte |
|---|---|---|---|
|  | MOV | L,A |  |
|  | INR | M | ; Increment memory |
|  | JZ | Label 1 | ; Check for overflow |
|  | INX | SP | ; Reset stack pointer |
|  | INX | SP |  |
|  | MVI | A, EOII | ; End-of-Interrupt |
|  | OUT | EOI |  |
|  | EI |  | ; Enable Interrupts |
|  | HLT |  | ; Stop the Processor |

If the first word overflowed, increment the second word.

| Label 1: | INR | H | ; Select second page |
|---|---|---|---|
|  | INR | M | ; Increment memory |
|  | MOV | A,M |  |
|  | DCR | H | ; Reset page pointer |
|  | CMP | D | ; Compare memory valve ; With preset limit |
|  | JZ | Label 2 | ; Check for overflow |
|  | INX | SP |  |
|  | INX | SP | ; Reset Stack pointer |
|  | MIV | A, EOII |  |
|  | OUT | EOI | ; End-of-interrupt |
|  | EI |  | ; Enable interrupts |
|  | HLT |  | ; Stop the processor |
| Label 2: | Calculations program. |  |  |

The data processing is basically evolved as follows. The computer is instructed to look over a certain number of the high energy characterizations in which the backscatter peak energy is probably to be found. The appropriate defined characterizations are thus scanned by the computer, and the characterization with the highest numerical count is chosen as the peak center line (accurate to plus or minus 1 characterization). This characterization or channel is hence the backscatter numerical count maximum. The program then requires the micro-computer to interpolate to develop a refined backscatter peak maximum herein also referred to as the refined backscatter peak center line, stated to at least 1/10 of a characterization or channel.

Interpolation is performed by requiring the computer to locate the characterizations or channel numbers near the backscatter peak maximum which have progressively 50, 60, 70 and 80 percent of the count recorded in the maximum channel (as illustrative examples). The principle thus relies on the development, by adequate data gathering, of a statistically reliable bell shape count distribution. Assuming for illustration that the 50 percent count lies in characterization of channels 140 and 219 respectively, and that the count maximum in channel 179, interpolation is performed as follows: 140+(219−140)/2=179.5= a first refined backscatter peak centerline. The procedure is repeated at a suitable number of percentages, such as 60, 70 and 80 percent, as mentioned, and the refined values are added, and then divided by the denominator equaling the number of such exercises performed, to arrive at the value of the refined backscatter peak center line. From this value, and the appropriate textbook constant, the fluorescence peak center line is determined, and the peak areas integrated, and the calculations performed in the traditional mode to arrive at the desired sample/matrix concentration value. As is readily apparent, however, the technique is broadly applicable to essentially any nuclear pulse counting experiment.

Examples

Preferred experimental apparatus is basically as diagrammed in FIG. 1. Hardware for the front end includes the conventional $^{109}$Cd source, Ar–CO$_2$ proportional counter, Canberra 806 preamp, Ortec 485 amp, and Ortec 456 high voltage power supply. The micro end includes the preferred components identified, supra.

What is observed as a critical parameter of the experimental system is the ADC zero stability, i.e., channel O of the ADC should correspond to zero energy. When zero energy is in channel zero, gain shifts caused by amp, preamp, or high voltage drift will cause the peaks in the spectrum to shift. However, the peak position ratios with respect to each other will not change. Table II lists the peak positions, in channel numbers, for a bromine fluorescence peak and the backscatter peak at various amplifier gains. Note column four, the ratio of the two peak positions. Also note that peak locations are determined to a fraction of a channel using interpolative procedures as described. The applicability of the interpolative procedures is critical, since the 256 channel resolution would be insufficient to provide completely accurate results if locations and energy windows were set only to the nearest whole channel. The simplest calculation will be the ratio of the area of the fluorescence peak to the area of the backscatter peak. Table III lists the peak areas and peak area ratios for the spectra listed in Table II. As the calculations show precision is excellent even under the variable and drastic gain variances used in the experiment.

Figure 5:
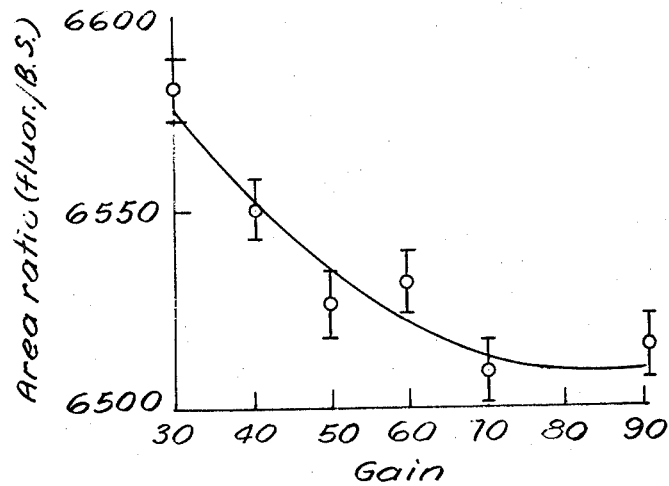
FIG. 5 is a plot of certain experimental data showing the relationship between amplification gain and peak area ratios.

Also to be considered with Tables II and III is the plot of FIG. 5 which shows the relationship between backscatter channel numbers or characterizations and peak area ratios. As the gain increases and the peaks move toward higher energy (higher channel number) the ratio decreases. This effect can be corrected by applying a correction factor to the peak area ratios, the value of the factor depending on the backscatter peak position. With the correction factor, the precision of the data listed in Table II would be at the theoretical limit, even under the difficult conditions of this experiment.

TABLE II

PEAK POSITION RATIO VS. AMPLIFIER GAIN
(Data Collected on Bromine Containing Polymer)

| Gain | B.S. Peak Channel No. | Fluorescence Peak Channel No. | Ratio (Fluor/B.S.) |
|---|---|---|---|
| 30 | 70.98 | 40.93 | 0.5766 |
| 40 | 94.00 | 54.16 | 0.5762 |
| 50 | 119.42 | 68.83 | 0.5761 |
| 60 | 142.57 | 82.10 | 0.5758 |
| 70 | 165.81 | 95.50 | 0.5760 |
| 80 | 188.84 | 108.76 | 0.5760 |
| 90 | 211.94 | 122.06 | 0.5759 |
| | | Average: | 0.5761 |
| | | 2σ (%) = | 0.09 |

TABLE III

PEAK AREA RATIOS AT VARIOUS AMP GAINS
(Data Collected on Bromine Containing Polymer)

| Gain | B.S. Area | Fluorescence* Peak | Area Ratios (Fluor/B.S.) |
|---|---|---|---|
| 30 | 488368 | 321427 | 0.6582 |
| 40 | 635894 | 416567 | 0.6551 |
| 50 | 799092 | 521395 | 0.6525 |
| 60 | 951371 | 621368 | 0.6531 |
| 70 | 1095700 | 713085 | 0.6508 |
| 80 | 1242110 | 808162 | 0.6506 |
| 90 | 1389640 | 905196 | 0.6514 |
| | | Average: | 0.6531 |
| | | SD$_x$ | 0.0027 |
| | | 2σ (%) = | 0.84 |
| | | Theor., 2σ (%) = | 0.32 |

*Integration limits are at 50% of peak max.

Under normal operating conditions, gain changes due to drift in the high voltage supply, preamp, and amp are more realistically considered to be approximately 10%. The stability studies of Tables IV and V list data collected on different days, with the same amplifier gain. Any peak shift is due principally to electronics drift. The data is collected using a bromine containing polymer as the sample (Table IV), and Uranium Sample in Water (Table V). The amplifier gain setting, peak locations, and ratio of fluorescence area to backscatter area is listed. As the data confirms, precision exceeds the theoretical nuclear decay statistical limit, under this set of more typical and probable amplifier gain parameters.

TABLE IV

AREA RATIOS AND PEAK AREAS AT CONSTANT GAIN
(Gain = 65, Data Collected on Bromine Containing Polymer)

| B.S. Peak Position | B.S.Peak* Area | Fluor. Peak* Area | Area Ratio (Fluor/B.S.) |
|---|---|---|---|
| 154.23 | 1025110 | 666816 | 0.6505 |
| 154.23 | 1025970 | 666202 | 0.6493 |
| 154.20 | 1027860 | 668462 | 0.6503 |
| 154.22 | 1017780 | 662802 | 0.6512 |
| 154.28 | 1021210 | 665365 | 0.6515 |
| 154.32 | 1024730 | 667247 | 0.6511 |
| 154.36 | 1025550 | 666452 | 0.6498 |
| 154.35 | 1026890 | 666608 | 0.6492 |
| 154.35 | 1023850 | 665675 | 0.6502 |
| 154.35 | 1016170 | 659705 | 0.6492 |
| | | Average: | 0.6502 |
| | | SD$_x$ = | 0.0008 |
| | | 2σ = | 0.26% (rel.) |
| | | Theoretical = | 0.31% (rel.) |

*Integration limits at 50% of peak max.

TABLE V

PEAK AREAS AND AREA RATIOS
378 ppm Uranium in Water
(5 Determinations)

| B.S. Peak Area | Fluorescence Peak Area | Ratio (Fluor/B.S.) |
|---|---|---|
| 1105270 | 100096 | 0.09056 |
| 1107460 | 99767 | 0.09009 |
| 1108940 | 100311 | 0.09046 |
| 1114100 | 101020 | 0.09067 |
| 1105210 | 100088 | 0.09056 |
| | Average: | 0.09047 |
| | 2σ = | 0.00045 |
| | = | 0.50 |
| | 2σ(Theoretical) = | 0.66% |

Similar excellent results are produced in analysis of streams for naturally occurring radioactive compounds in water, in which experiment, the detector is immersed in the stream being monitored. Backscatter is not present because of the inherent radioactive decay of the sample species. The decay count, however, is quantitable by the technique of the invention, and compared with standards to precisely deduce the concentration of the naturally occurring radioactive element in the stream.

What is claimed is:

1. In a nuclear pulse counting experiment wherein pulse charges are developed pursuant to a detection step, and converted to amplified voltage pulses proportional to the magnitude of the pulse charges, the method of tabulating such voltage pulses, occurring in a specified energy range, and defining the energy peak center, comprising the steps of: sorting the voltage pulses into at least 128 characterizations according to magnitude, said sorting function being performed essentially without compensation for meandering amplification gain shifts, discontinuing the experiment based on a statistically reliable counting of a numerically sufficient sample of pulse charges, determining that characterization containing the maximum count, ±1 characterization, and defining that characterization as the energy peak center, interpolating to refine the energy peak center to an accuracy of at least 1/10 of a characterization, and tabulating the numerical count of the pulse charges based on the refined energy peak center.

2. An X-ray fluorescence analysis performed according to the method of claim 1 to determine sample/matrix quantitative data, wherein the energy peak center of the backscatter is defined according to the mode therein described.

3. The method of claim 2 wherein the step of terminating data gathering is based on a specified count occurring in any one characterization, and wherein that characterization is defined as the energy peak center.

4. The method of claim 2 wherein the voltage pulses are sorted into at least 256 characterizations, said experiment being distinguished by a precision expressed by the theoretical nuclear decay statistical limit.

5. The method of claim 4 including the step of regulating the frequency of the transmission of the characterized voltage pulses.

* * * * *

UNITED STATES PATENT AND TRADEMARK OFFICE
CERTIFICATE OF CORRECTION

PATENT NO. : 4,228,512
DATED : October 14, 1980
INVENTOR(S) : John W. Thompson et al.

It is certified that error appears in the above—identified patent and that said Letters Patent is hereby corrected as shown below:

In the Abstract, line 2, delete "empolys" and insert --employs--.

Column 2, line 6, delete "predicted" and insert --predicated--.

Column 5, line 30, delete the word "fit" and insert --bit--.

Column 6, Table I, under Label 1, first column, delete "MIV" and insert --MVI--.

Column 8, Table V, Item 8 of the last column, insert --%-- after "0.50".

Signed and Sealed this

Third Day of March 1981

[SEAL]

Attest:

Attesting Officer

RENE D. TEGTMEYER

Acting Commissioner of Patents and Trademarks